(12) United States Patent
Kim et al.

(10) Patent No.: US 10,662,407 B2
(45) Date of Patent: May 26, 2020

(54) METHOD FOR CONTROLLING DIFFERENTIATION OF EMBRYONIC STEM CELLS INTO ADIPOCYTES OR KIDNEY PRECURSOR CELLS BY REGULATING SIRT1 EXPRESSION

(71) Applicants: INDUSTRIAL COOPERATION FOUNDATION CHONBUK NATIONAL UNIVERSITY, Jeollabuk-do (KR); CHONBUK NATIONAL UNIVERSITY HOSPITAL, Jeollabuk-do (KR)

(72) Inventors: Won Kim, Jeollabuk-do (KR); Yu Jin Jung, Jeollabuk-do (KR)

(73) Assignees: INDUSTRIAL COOPERATION FOUNDATION CHONBUK NATIONAL UNIVERSITY, Jeollabuk-Do (KR); Chonbuk National University Hospital, Jeollabuk-Do (KR)

( * ) Notice: Subject to any disclaimer, the term of this patent is extended or adjusted under 35 U.S.C. 154(b) by 0 days.

(21) Appl. No.: 15/546,634

(22) PCT Filed: Jan. 22, 2016

(86) PCT No.: PCT/KR2016/000721
§ 371 (c)(1),
(2) Date: Dec. 18, 2017

(87) PCT Pub. No.: WO2016/122166
PCT Pub. Date: Aug. 4, 2016

(65) Prior Publication Data
US 2018/0179491 A1    Jun. 28, 2018

(30) Foreign Application Priority Data

Jan. 26, 2015   (KR) .................. 10-2015-0012049
Jun. 24, 2015   (KR) .................. 10-2015-0089783
Jan. 21, 2016   (KR) .................. 10-2016-0007611

(51) Int. Cl.
*C12N 5/0735* (2010.01)
*C12N 5/077* (2010.01)
*C12N 5/071* (2010.01)
*A61K 35/22* (2015.01)

(52) U.S. Cl.
CPC ......... *C12N 5/0606* (2013.01); *C12N 5/0653* (2013.01); *C12N 5/0686* (2013.01); *A61K 35/22* (2013.01); *C12N 2501/01* (2013.01); *C12N 2501/16* (2013.01); *C12N 2501/235* (2013.01); *C12N 2501/24* (2013.01); *C12N 2501/33* (2013.01); *C12N 2501/375* (2013.01); *C12N 2501/385* (2013.01); *C12N 2501/39* (2013.01); *C12N 2501/998* (2013.01); *C12N 2501/999* (2013.01); *C12N 2506/02* (2013.01)

(58) Field of Classification Search
CPC .................................................. C12N 5/0606
See application file for complete search history.

(56) References Cited

U.S. PATENT DOCUMENTS

2011/0218229 A1   9/2011   Guarente et al.
2013/0302290 A1   11/2013  Amrani et al.

FOREIGN PATENT DOCUMENTS

KR   10-2012-0128451 A   11/2012

OTHER PUBLICATIONS

Safaeinejad et al. (2018, European J. Med. Chem., vol. 155, pp. 651-657) (Year: 2018).*
Zhou et al., 2017, Mol. Med. Reports, vol. 16, pp. 2969-2975 (Year: 2017).*
Durand et al. (2011, Viruses, vol. 3, pp. 132-159) (Year: 2011).*
Liu et al. (2016, Stem Cells Int., Article ID 2524092, pp. 1-11) (Year: 2016).*
Hwang et al., 2008, Adv. Drug Deliv. Rev., vol. 60(2), pp. 199-512 (Year: 2008).*
Yoo et al., 2014, Scientific Reports, vol. 4, pp. 1-8 (Year: 2014).*
Whyatt et al. (1993, Molecular and Cellular Biology, vol. 13(12), pp. 7971-7976) (Year: 1993).*
Srivastava et al. (2012, Molecular and Cellular Endocrinology, vol. 361, pp. 153-164). (Year: 2012).*
International Search Authority/KR, International Search Report dated May 18, 2016 in International Patent Application No. PCT/KR2016/000721(with English translation), 8 pages.
Demetrius M. Kokkinakis et al., "Modulation of Gene Expression in Human Central Nervous System Tumors under Methionine Deprivation-induced Stress", American Association for Cancer Research, vol. 64, p. 7513-7525, Oct. 15, 2004.
Homayoun Vaziri et al., "hSIR2SIRT1 Functions as an NAD-Dependent p53 Deacetylase", Cell, vol. 107, p. 149-159, Oct. 19, 2001, Copyright (c) 2001 by Cell Press.

(Continued)

*Primary Examiner* — Thaian N. Ton
*Assistant Examiner* — David A. Montanari
(74) *Attorney, Agent, or Firm* — Masuvalley & Partners

(57) ABSTRACT

The present disclosure relates to a method for controlling the differentiation of embryonic stem cells into adipocytes or kidney precursor cells by regulating SIRT1 (silent mating type information regulation 2 homolog; sirtuin 1) expression, the method, which controls the differentiation of embryonic stem cells into adipocytes by regulating SIRT1 expression, being capable of controlling the inhibition or promotion of adipocyte differentiation in accordance with the timing of a SIRT1 expression inhibitor treatment. Furthermore, kidney precursor cell differentiation can be regulated by a SIRT1 expression inhibitor or promoter treatment. Accordingly, a SIRT1 inhibitor can be selected to be used as an inhibitor or a therapeutic agent for obesity, diabetes accompanying obesity, and renal and metabolic diseases.

8 Claims, 9 Drawing Sheets

Specification includes a Sequence Listing.

(56) References Cited

OTHER PUBLICATIONS

Danica Chen et al., "Increase in Activity During Calorie Restriction Requires Sirt1", Science vol. 310, p. 1641, Dec. 9, 2005, www.sciencemag.org.
Frederic Picard et al., "Sirt1 promotes fat mobilization in white adipocytes by repressing PPAR-γ", Published in final edited form as:Nature. Jun. 17, 2004; 429(6993): 771. doi:10.1038/nature02583., p. 1-14.
Tianle Yang et al., "SIRT1 and endocrine signaling", Trends in Endocrinology and Metabolism vol. 17 No. 5 Jul. 2006, p. 186-191.

* cited by examiner

METHOD FOR CONTROLLING DIFFERENTIATION OF EMBRYONIC STEM CELLS INTO ADIPOCYTES OR KIDNEY PRECURSOR CELLS BY REGULATING SIRT1 EXPRESSION

RELATED APPLICATIONS

This application is a U.S. National Phase application under 35 U.S.C. § 371 of International Patent Application No. PCT/KR2016/000721 filed on Jan. 22, 2016, which claims priority to Korean Patent Application No. 10-2015-0012049 filed on Jan. 26, 2015, Korean Patent Application No. 10-2015-0089783 filed on Jun. 24, 2015, and Korean Patent Application No. 10-2015-0007611 filed on Jan. 21, 2016, which are hereby expressly incorporated by reference in their entirety for all purposes.

BACKGROUND

1. Field of the Disclosure

The present disclosure relates to a method for controlling differentiation of embryonic stem cells into adipocytes or kidney precursor cells, which comprises regulating an expression of silent mating type information regulation 2 homolog: sirtuin 1 (SIRT1), and more particularly, to a method for inhibiting the differentiation of the embryonic stem cells into the adipocyte or the kidney precursor cells, which comprises inhibiting the expression of SIRT1.

2. Discussion of Related Art

Silent mating type information regulation 2 homolog: sirtuin 1 (SIRT1) is a NAD+ dependent deacetylase that is known to be an enzyme that regulates protein function by deacetylating lysine residues of various proteins (Aging Res, Vol. 1, p. 313-326, 2002), which is most similar to Sir2 of yeast, having NAD+ dependent class III histone deacetylase activity. In particular, it is known that it cleaves acetyl groups attached to transcription factors such as Nuclear factor-kB and p53, and controls their functions (Cancer Res, Vol. 64, pp. 7513-7525, 2004, Cell, Vol. 107, Trends Endocrinol Metab, Vol. 17, pp. 186-191, 2006).

SIRT1 is involved in DNA damage response, prolonged lifespan associated with dietary restrictions, and chromatin reconstitution, associated with gene expression inhibition (Chen et al., Science, 310: 1641, 2005). In other words, SIRT1 reconstitutes chromatin through histone deacetylation, inhibits gene expression, induces the deacetylation of various transcription factors related to cell growth, stress response, and endocrine regulation in addition to histone protein. Further, according to recent studies, it has been reported that SIRT1 increases the deacetylation activity of SIRT1, and thus it has been applied to the treatment of diabetes, obesity, neurodegenerative diseases or aging-related diseases, and it has been reported that SIRT1 inhibits the expression of PPAR-γ, and thus inhibits differentiation into adipocyte (Frederic Picard et al., Nature, 429: 771, 2004), however, there have been no studies on controlling of adipocyte differentiation by regulating the expression of SIRT1 in embryonic stem cells.

Accordingly, the present inventors have made intensive efforts to develop a method of controlling differentiation into an adipocyte or a kidney precursor cell by regulating the expression of SIRT1 in an embryonic stem cell. As a result, it was confirmed that Silent mating type information regulation 2 homolog: sirtuin 1 (SIRT1) is involved in differentiation of an embryonic stem cell into an adipocyte or a kidney precursor cell, and the differentiation into an adipocyte or a kidney precursor cell may be inhibited or promoted according to the SIRT1 expression inhibition time. Thus completing examples of the present disclosure.

SUMMARY OF THE DISCLOSURE

It is an object of the present disclosure to provide a method for inhibiting or promoting the differentiation of an embryonic stem cell into an adipocyte or a kidney precursor cell through regulating of silent mating type information regulation 2 homolog; sirtuin 1 (SIRT1) expression.

In order to solve the above-mentioned problems, a method for inhibiting differentiation of an embryonic stem cell into an adipocyte or a kidney precursor cell may include inhibiting a expression of SIRT1.

In a preferred embodiment of the present disclosure, the method may further include inhibiting the differentiation of the embryonic stem cell into the adipocyte or the kidney precursor cell by treating a SIRT1 expression inhibitor with an embryoid body formed by culturing the embryonic stem cell.

In a preferred embodiment of the present disclosure, the SIRT1 expression inhibitor may be treated for 0 to 7 days at the early stage of the culturing the embryoid body.

In a preferred embodiment of the present disclosure, the SIRT1 expression inhibitor may be one selected from the group consisting of 2-[(2-Hydroxynaphthalen-1-ylmethylene)amino]-N-(1-phenethyl)benzamide (Sirtinol), a pyridine-3-carboxamide (Nicotinamide), and 6-Chloro-2,3,4,9-tetrahydro-1H-Carbazole-1-carboxamide (EX527).

In a preferred embodiment of the present disclosure, mRNA expressions of a peroxisome proliferator-activated receptors-γ (PPAR-γ), a CCAAT/enhancer-binding protein-α (C/EBP α), a fatty acid binding protein 4 (FABP4), a sine oculis homeobox homolog 2 (SIX2), and a wilms tumor 1 (WT1) may be decreased.

Another object of the present disclosure may provide a method for promoting differentiation of an embryonic stem cell into an adipocyte. The method may include (a) forming an embryoid body by culturing an embryonic stem; and (b) inducing differentiation into adipocyte by culturing the embryoid body in a medium containing a SIRT1 expression inhibitor.

In a preferred embodiment of the present disclosure, the SIRT1 expression inhibitor may be treated for 7 to 21 days in the differentiation induction in step (b).

In a preferred embodiment of the present disclosure, the SIRT1 expression inhibitor may be one selected from the group consisting of 2-[(2-Hydroxynaphthalen-1-ylmethylene)amino]-N-(1-phenethyl)benzamide (Sirtinol), a pyridine-3-carboxamide (Nicotinamide), and 6-Chloro-2,3,4,9-tetrahydro-1H-Carbazole-1-carboxamide (EX527).

In a preferred embodiment of the present disclosure, the medium of step (b) may be a medium for inducing differentiation into adipocytes, and may comprise at least one substance selected from the group consisting of insulin, triiodothyronine, and rosiglitazone.

Another object of the present disclosure may provide a method for promoting differentiation of an embryonic stem cell into a kidney precursor cell. The method may include promoting differentiation into kidney precursor cells by treating an embryonic stem cell with a SIRT1 expression promoter.

In a preferred embodiment of the present disclosure, the SIRT1 expression promoter may be provided for 0 to 21 days from the induction of differentiation and most preferably may be provided from 1 to 7 days.

In a preferred embodiment of the present disclosure, the SIRT1 expression promoter may be at least one selected from the group consisting of SRT1270 (ChemCruz Biochemicals), adenovirus, lentivirus, BML-278 (ChemCruz Biochemicals) and resveratrol, and preferably, may be resveratrol. The SIRT1 expression promoter may be added to the medium at a concentration of 10 to 50 μM.

According to another preferred embodiment of the present invention, mRNA expression level of SIX2 (sine oculis homeobox homolog 2) and WT 1 (wilms tumor 1) of embryonic stem cell is increased due to SIRT1 expression promoter, from which it can be confirmed that the differentiation into a kidney precursor cell is promoted (FIG. 3 and FIG. 4).

According to another preferred embodiment of the present invention, the medium is a medium for inducing differentiation into a kidney precursor cell, and may include one or more substances selected from the group consisting of retinoic acid ((2E,4E,6E,8E)-3,7-dimethyl-9-(2,6,6-trimethylcyclohexen-1-yl)nona-2,4,6,8-tetraenoic acid) and activing A.

It is an object of the present disclosure to provide a kidney cell.

It is an object of the present disclosure to provide a renal function remedy and therapeutic agent comprising a kidney precursor cell Since the method for controlling differentiation of the embryonic stem cell into the adipocyte or the kidney precursor cell by regulating the expression of SIRT1 according to the present disclosure can control the inhibition or promotion of differentiation into the adipocyte or the kidney precursor cell according to the treatment time of a SIRT1 expression inhibitor, by selecting the SIRT1 inhibitor, the cell thus obtained can be used as an inhibitor or therapeutic agent in the treatment of obesity, obesity-associated diabetes, kidney disease, and metabolic disease.

DETAILED DESCRIPTION OF EXEMPLARY EMBODIMENTS

Figure 1:
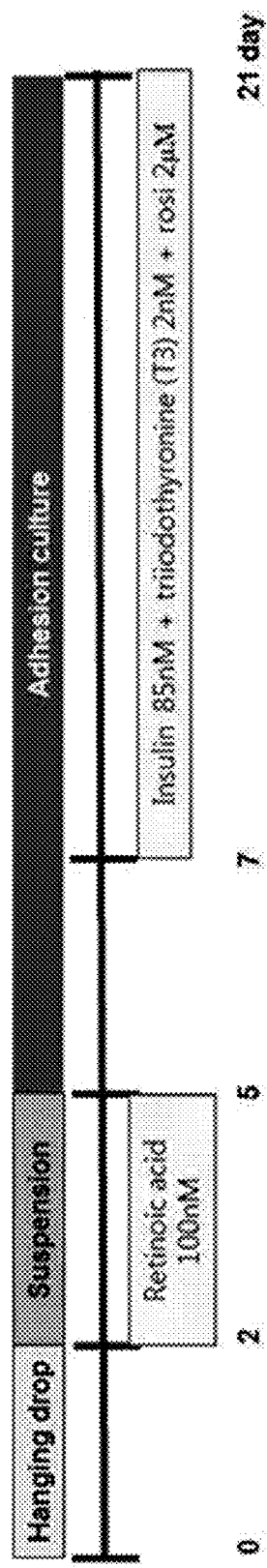
FIG. 1 is schematic diagram illustrating a culture protocol for differentiating into embryonic stem cell into an adipocyte.

Hereinafter, the present disclosure will be described in more detail.

As described above, various studies have been carried out on the function of silent mating type information regulation 2 homolog: sirtuin 1 (SIRT1) gene, and it has been reported that when SIRT1 expression increases, PPAR-y expression is inhibited and inhibits differentiation into adipocytes. However, there have been no studies on the regulation of differentiation into adipocytes or caprine progenitor cells according to the regulation of SIRT1 expression in embryonic stem cells.

The present disclosure seeks to solve the above-mentioned problem by providing a method of controlling differentiation of adipocytes or kidney precursor cells of embryonic stem cells by regulating an expression of SIRT1. SIRT1 is involved in the differentiation of embryonic stem cells into adipocytes or kidney precursor cells, it was confirmed that differentiation into adipocyte or kidney precursor cells was inhibited or promoted according to the inhibition phase of SIRT1 expression, unlike previous knowledge in the art, there is an effect that can be used as a model for the study of childhood obesity, a study model of kidney disease according to the regulation of SIRT1 expression in an embryo through the method of controlling the differentiation of embryonic stem cells into adipocytes or kidney precursor cells.

Accordingly, the present disclosure relates to a method for controlling differentiation adipocytes or kidney precursor cells, the method comprises a step of inhibiting SIRT1 expression in an embryonic stem cell, particularly, comprises a method for inhibiting differentiation into adipocyte or kidney precursor cells by treating an embryoid body with a SIRT1 expression inhibitor when culturing embryonic stem cells.

The SIRT1 of the present disclosure is an abbreviation of silent mating type information regulation 2 homolog; sirtuin 1, and the sequence of the SIRT1 gene can be represented by SEQ ID NO: 1.

A "stem cell" of the present disclosure is a cell having an ability to be differentiated into various types of cells and having self-proliferative ability. Three types of an embryonic stem cell (ES cell) isolated from an early embryo, an embryonic germ cell (EG cells) isolated from primordial germ cells of the embryo, and a multipotent adult progenitor cell (MAPC cell) isolated from the adult bone marrow, are the most well-known.

In the present disclosure, a mouse-derived embryonic stem cell is used as an embryonic stem cell, but the present disclosure is not limited thereto. Examples of mouse-derived embryonic stem cells, particularly, include EB3 cells, E14 cells, D3 cells, CCE cells, R1 cells, 129SV cells and J1 Cells, and the like. In addition, these stem cells can be easily used for the preparation, passage and preservation of an embryonic stem cell, an embryonic germ cell and an multipotent adult progenitor cell with reference to a standard protocol already established (Matsui et al., Cell, 70: 841 1992. Shamblott et al. Proc. Natl. Acad. Sci. USA 95: 13726 1998. U.S. Pat. No. 6,090,622; Jiang et al., Nature, 418: 41, 2002; International Patent Publication WO 01/11011), and can be cultured using various known culture mediums for feeder cells and embryonic stem cells.

Cells usable in the present disclosure are not limited to embryonic stem cells but include the embryos of mammals or stem cells having similar characteristics to embryonic stem cells. In this case, the term "similar characteristics to embryonic stem cells" can be defined as cell-biologic characteristics specific to embryonic stem cells such as containing a surface (antigen) marker specific to embryonic stem cells, expression of an embryonic stem cell-specific gene, having a teratoma formation function, having a chimeric mouse-forming function, or the like.

The SIRT1 expression inhibitor may be supplied for 0 to 7 days in the culturing of an embryoid body, the SIRT1 expression inhibitor may be one or more selected from the group consisting of 2-[(2-Hydroxynaphthalen-1-ylmethylene)amino]-N-(1-phenethyl)benzamide (Sirtinol) and 6-Chloro-2,3,4,9-terahydro-1H-Carbazole-1-carboxamide (EX527).

Although EX527 is preferably used in the present disclosure, known SIRT1 expression inhibitors capable of inhibiting SIRT1 expression can be used without limitation, while sequences specific to SIRT1, such as siRNA, which inhibits the protein synthesis of SIRT1, can be synthesized and used.

When inhibiting differentiation into adipocytes, the SIRT1 expression inhibitor may be added to the medium at a concentration of 5 to 500 μM, preferably 10 to 100 μM, and when added at a concentration of 5 μM or less, there may be no effect of inhibiting differentiation into the adipocytes, when added at a concentration of 500 μM or more, cytotoxicity may be exhibited or there may be a problem that the efficiency is decreased because the improvement in the effect according to a Concentration increase is small.

When inhibiting differentiation into a kidney precursor cell, the SIRT1 expression inhibitor may be added to the medium at a concentration of 4 to 25 μM, preferably 5 to 10 μM, and when added at a concentration of 5 μM or less, there may be no effect of inhibiting differentiation into the kidney precursor cell, when added at a concentration of 500 μM or more, cytotoxicity may be exhibited or there may be a problem that efficiency is decreased because the improvement in the effect according to a Concentration increase is small.

In the example of the present disclosure, R1, a mouse embryonic stem cell, was used, and in order to determine whether the differentiation of embryonic stem cells into adipocytes depended on the presence or absence of SIRT1 protein expression, a control group as a SIRT1 gene-expressing mouse embryonic stem cell (SIRT1+/+; WT) and a mouse embryonic stem cell (SIRT1−/−; KO) lacking the SIRT1 gene was prepared, the SIRT1 gene-expressing mouse embryonic stem cell were treated with the SIRT1 inhibitor EX527, and a degree of lipid differentiation by SIRT1 inhibition was confirmed.

In the present disclosure, a method of a hanging-drop culture is preferably used in order to form an embryoid body by culturing an embryonic stem cell. However, methods for forming an embryoid body known in the art can be used without limitation.

1) Inhibition of Differentiating into Adipocyte

FIG. 1 is a schematic diagram showing a culture protocol for differentiating an embryonic stem cell into an adipocyte. In one example of the present disclosure, an embryoid body, formed by a hanging-drop culture method, was treated with Retinoic acid, and differentiation of adipocytes was induced by culturing in adipocyte differentiation medium containing insulin, Triiodothyronine and rosiglitazone, for 14 days.

As described above, as relates to the induction of differentiation of an embryonic stem cell into adipocyte, a group of SIRT1 gene-expressing mouse embryonic stem cells (SIRT1+/+; WT), a group of mouse embryonic stem cells (SIRT1−/−; KO) lacking the SIRT1 gene, and a group of SIRT1 gene-expressing mouse embryonic stem cells were divided for an identifying effect of SIRT1 on the differentiation into adipocytes.

Figure 2:
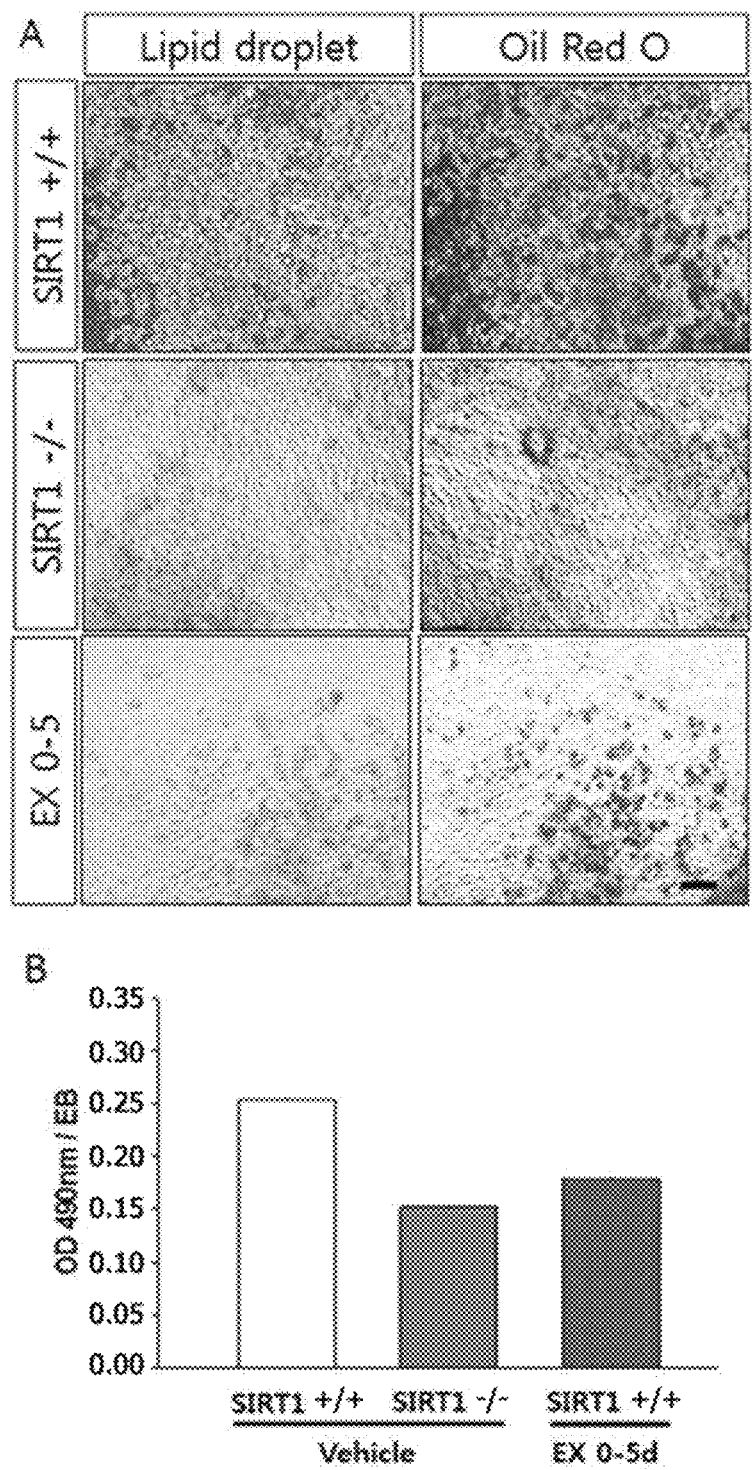
FIG. 2 is data showing the degree of differentiation of embryonic stem cells into adipocytes according to the presence or absence of SIRT1 expression (A: image showing lipid droplet formed in an adipocyte through oil red O staining, B: data of extracting an Oil red O stained sample and measuring absorbance).

FIG. 2 shows the degree of differentiation of an embryonic stem cell into an adipocyte according to the presence or absence of SIRT1 expression, as shown in FIG. 2A, in a SIRT1+/+ cells, embryonic stem cells were differentiated into adipocytes, and it was confirmed that many intracellular lipid droplets were formed, on the other hand, in SIRT1−/− cells, it was confirmed that there was almost no differentiation into adipocytes. In addition, when SIRT1+/+ cells were treated with the SIRT1 inhibitor EX527, partially lipid droplets were observed, but it was confirmed that adipocyte differentiation was remarkably lower than that of SIRT1+/+ cells. In other words, the inhibition of SIRT1 expression inhibited the differentiation into adipocytes.

FIG. 2B is data of measuring absorbance at 500 nm after extracting oil red O stained sample in lipid droplets of cells, it was confirmed that SIRT1−/− cells were reduced by 40% in differentiation into adipocytes compared to SIRT1+/+ cells, when EX527 which was SIRT1 inhibitor was treated, it was confirmed that adipocyte differentiation was reduced by about 38%.

In the present disclosure, mRNA expression of a peroxisome proliferator-activated receptors-γ (PPAR-γ), a CCAAT/enhancer-binding protein-α (C/EBP α) and a fatty acid binding protein 4 (FABP4) in embryonic stem cells can be suppressed by suppression of SIRT1 expression.

Figure 3:
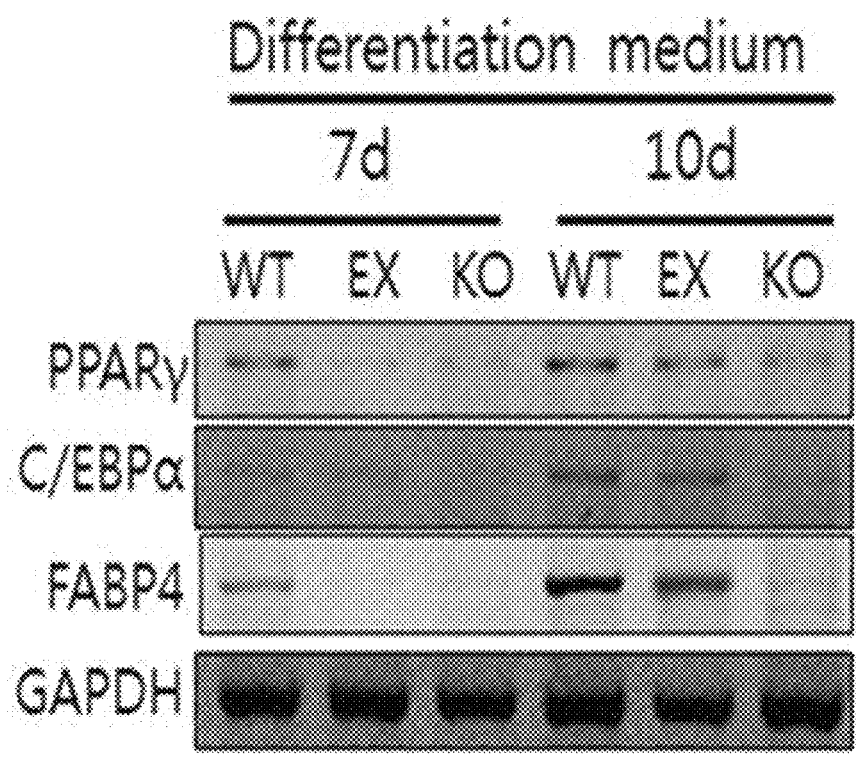
FIG. 3 is data showing degrees of mRNA expression of PPAR, C/EBPα and FABP4 according to the presence or absence of SIRT1 expression in inducing differentiation of an embryonic stem cell into an adipose stem cell.

In one example of the present disclosure, in order to investigate the mechanism of promoting lipid differentiation of SIRT1, mRNA expression level of PPARγ, C/EBP α and FABP4 in adipocytes were measured by PCR method, FIG. 3 is data of mRNA expression level of PPARγ, C/EBP α and FABP4 according to whether SIRT1 is expressed or not when it is induced differentiation of an embryonic stem cell into an adipose stem cell, it was confirmed that mRNA expressions of PPARγ, C/EBP α and FABP4 were increased in SIRT1+/+ cells after induction of differentiation into adipocytes, On the other hand, it was confirmed that mRNA expressions of PPARγ, C/EBP α and FABP4 were significantly decreased when SIRT1−/− cells and EX527 which was SIRT1 inhibitor were treated.

In other words, Unlike previous studies (Frederic Picard et al., Nature, 429: 771, 2004) in which SIRT1 inhibits the expression of PPAR-γ and inhibits differentiation into adipocytes, it was confirmed that mRNA expression of PPARγ was decreased by the inhibition of SIRT1 expression at the early stage of culture of embryoid body formed from embryonic stem cells.

2) Inhibition of Differentiation into Kidney Precursor Cell

In the example of the present disclosure, R1, a mouse embryonic stem cell, was used, and in order to determine whether the differentiation of embryonic stem cells into kidney precursor cells depended on the presence or absence of SIRT1 protein expression, control groups of a SIRT1 gene-expressing mouse embryonic stem cell (SIRT1+/+; WT) and a mouse embryonic stem cell (SIRT1−/−; KO) lacking the SIRT1 gene was prepared, the SIRT1 gene-expressing mouse embryonic stem cell were treated with the SIRT1 inhibitor EX527, and a degree of kidney precursor cell differentiation by SIRT1 inhibition was confirmed.

Figure 5:
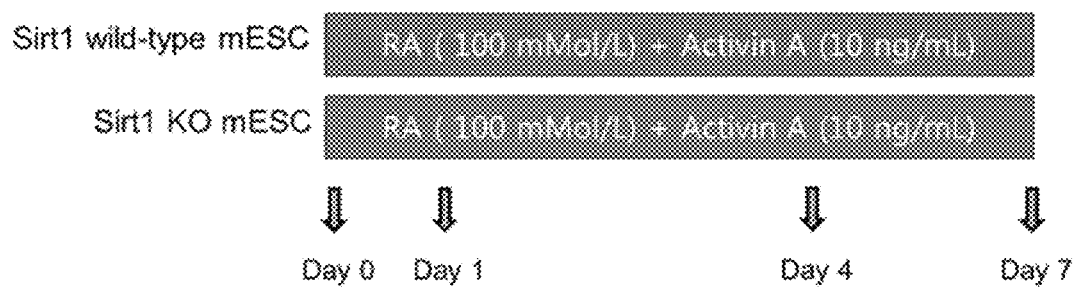
FIG. 5 is schematic diagram showing a culture protocol for differentiating of an embryonic stem cell into a kidney precursor cell (RA: retinoic acid).

FIG. 5 is a schematic diagram showing a culture protocol for differentiating embryonic stem cells into kidney precursor cells, in the example of the present disclosure, differentiation into caprine kidney precursor cells is led by providing retinoic acid (100 nmol/L) and Actin A (10 ng/mL) in a cell culture medium without Leukemia Inhibitory Factor (LIP; Milipore, USA) for 7 days.

As described above, relates to the induction of differentiation of an embryonic stem cell into a kidney precursor cell, a group of SIRT1 gene-expressing mouse embryonic stem cells (SIRT1+/+; WT) and a group of mouse embryonic stem cells (SIRT1−/−; KO) lacking the SIRT1 gene were divided for an identifying effect of SIRT1 on the differentiation into kidney precursor cell.

In the present disclosure, inhibition of SIRT1 expression in embryonic stem cells by inhibition of SIRT1 expression inhibited the mRNA expression level of sine oculis homeobox homolog 2 (SIX2) and wilms tumor 1 (WT1) in embryonic stem cells, whereby it may be that differentiation into kidney precursor cells is inhibited.

Figure 6:
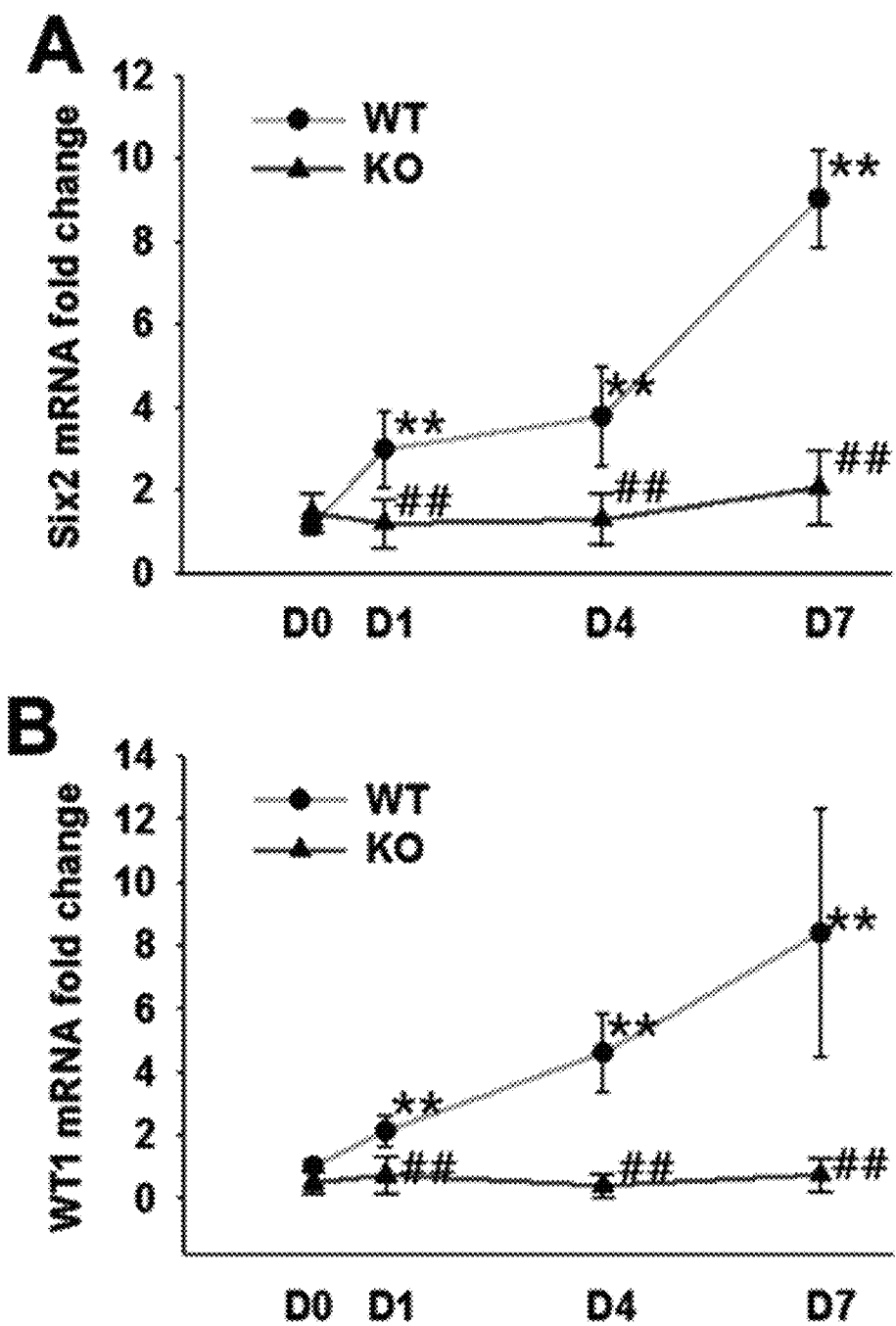
FIG. 6 is data of mRNA expression degree of Six2 and WT1 which are kidney precursor cell indicators after differentiation of SIRT1 protein expressing cells (SIRT1+/+; WT) and non-SIRT1 protein expressing cell (SIRT1−/−; KO).

In the example of the present disclosure, in order to investigate the inhibition of kidney precursor cell differentiation of SIRT1, the mRNA expression levels of intracellular Six2 and WT1 were measured by a PCR method, and the result is shown in FIG. 2. FIG. 6 is data of mRNA expression degree of Six2 and WT1 according to whether SIRT1 is expressed or not when it is differentiation of embryonic stem cells into adipose stem cells was induced, in SIRT1+/+ cells, it was confirmed that mRNA expressions of Six2 and WT1 were increased after the induction of differentiation into kidney precursor cells, on the other hand, it was confirmed that mRNA expressions of Six2 and WT1 were significantly inhibited in SIRT1−/− cells.

The method for controlling adipocyte differentiation of an embryonic stem cell of the present disclosure also comprises a method for promoting differentiation of an embryonic stem cell into an adipocyte, and the method for promoting differentiation of an embryonic stem cell into an adipocyte comprises:

(a) forming an embryoid body by culturing an embryonic stem cell; and (b) inducing differentiation into adipocyte by culturing the embryoid body in a medium containing SIRT1 expression-regulating substance, in step (B), the SIRT1 expression-regulating substance may be a SIRT1 expression inhibitor and the induction of differentiation may be treated for 7 to 21 days.

Figure 4:
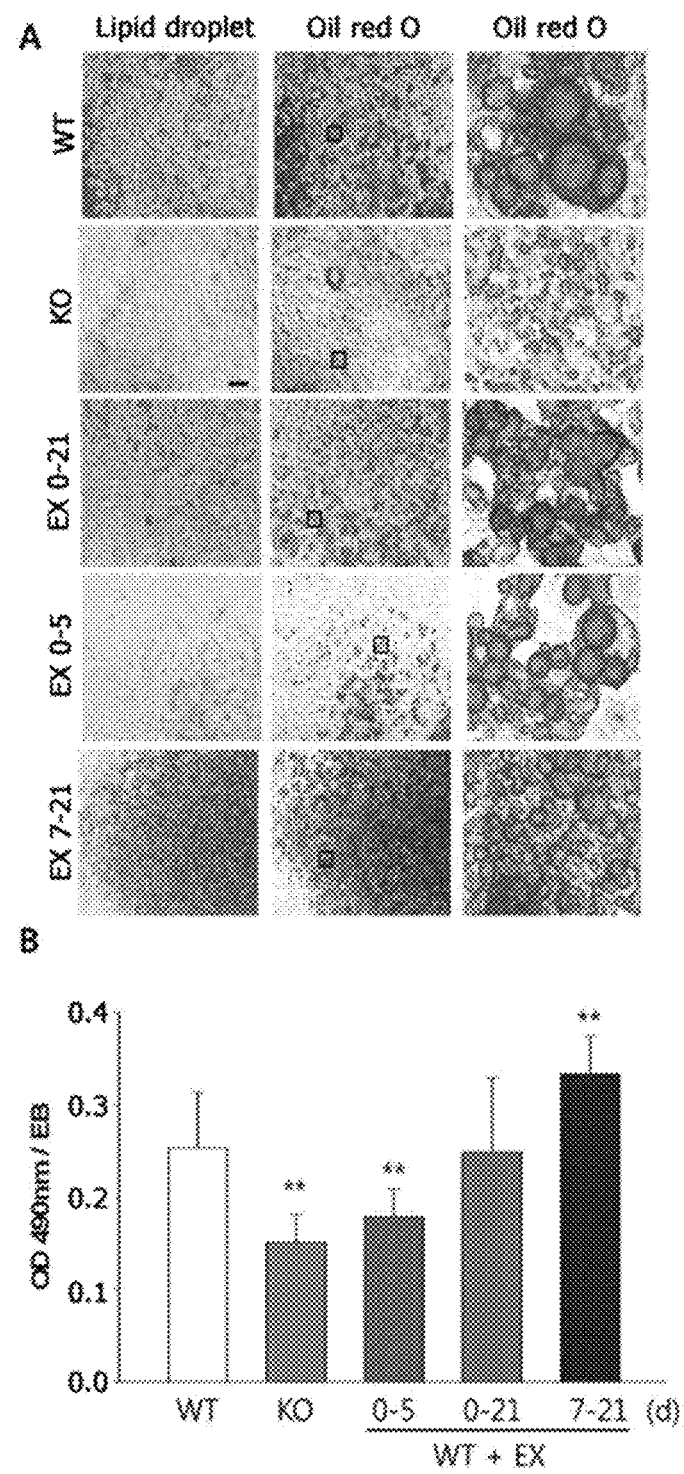
FIG. 4 is data showing the degree of differentiation of an embryonic stem cell into an adipocyte according to treatment time of SIRT1 expression inhibitor (A: image showing lipid droplet formed in adipocyte through oil red O staining, B: data of extracting an Oil red O stained sample and measuring absorbance).

In one example of the present disclosure, a result of confirming the effect on differentiation into adipocytes according to time (or period) of inhibition of SIRT1 expression, as shown in FIG. 4, it was confirmed that a group treated with an SIRT1 inhibitor only at the early stage of differentiation showed a decrease in differentiation into adipocytes as compared to the group treated with inhibitor, a group treated with an SIRT1 inhibitor during the entire differentiation period was not significantly different from a group without an inhibitor treatment, and a group treated with an inhibitor for 7-21 days in which the latter stage of differentiation was more differentiated into adipocytes than the group without inhibitor treatment.

It was confirmed that the method for controlling the differentiation of embryonic stem cell into adipocytes, in the present disclosure, can induce the inhibition or promotion of differentiation into adipocytes according to the time of inhibition of SIRT1 expression, and it was confirmed that differentiation into adipocytes was inhibited by inhibition of SIRT1, unlike previously known cases when SIRT1 expression was inhibited at the early stage culturing of embryoid body formed from embryonic stem cells, and it was confirmed that differentiation into adipocytes was promoted when SIRT1 expression was inhibited during 7 to 21 days in the induction of differentiation of the embryoid body into adipocytes.

Therefore, a method for controlling differentiation of embryonic stem cells into adipocytes by regulating SIRT1 expression of the present disclosure, since inhibition or promotion of differentiation of adipocyte can be controlled depending on the treatment time of SIRT1 expression inhibitor, can be used as an model of studying childhood obesity and the like, according to the inhibition time of SIRT1 expression in an embryo.

In the present disclosure, in order to promote differentiation from embryonic stem cells into adipocytes, the SIRT1 expression promoter may be provided for 0 to 5 days for inducing differentiation, instead of the SIRT1 inhibitor in step (b), the SIRT1 expression promoter may be one or more selected from the group consisting of interferon beta-1a, interferon beta-1b, cyclic guanosine monophosphate (cGMP), adiponectin, pyruvate, 2-deoxyglucose, SRT1270 (ChemCruz Biochemicals), adenovirus, lentivirus, BML-278 (ChemCruz Biochemicals) and resveratrol, materials known in the art as being capable of promoting or inducing SIRT1 expression can be used without limitation.

The present disclosure also includes an adipocyte prepared by the method for promoting differentiation into adipocytes and a composition for regenerating tissue containing the adipocytes as an active ingredient.

A composition for regenerating tissue containing the adipocytes induced from the embryonic stem cell of the present disclosure as an active ingredient can be formulated by a known method in the pharmaceutical field, it may be formulated into various formulations such as a conventional pharmaceutical preparation, for example, a liquid preparation, an ointment, an emulsion, a gel, a cream preparation, a paste preparation and the like by mixing a structure with a pharmaceutically acceptable carrier, excipient and the like, or the structure itself.

The dose of the therapeutic agent for tissue regeneration of the present disclosure is not particularly limited, the preferred dosage depends on the condition and the weight of the patient, the condition or degree of disease, the type of drug and the period of time, but can be appropriately selected by a person skilled in the art. For the desired effect, the therapeutic agent of the present disclosure is usually administered at 25 to 100 μM, preferably 45 to 65 μM per wound per day. The administration can be administered once to several times a day.

The present disclosure provides a method for promoting differentiation of embryonic stem cells into kidney precursor cells, which comprises promoting the differentiation into kidney precursor cells by treating embryonic stem cells with a SIRT1 expression promoter.

The SIRT1 expression promoter may be selected one or more from the group consisting of interferon beta-1a, interferon beta-1b, cyclic guanosine monophosphate (cGMP), adiponectin, pyruvate, 2-deoxyglucose, SRT1270 (ChemCruz Biochemicals), adenovirus, lentivirus, BML-278 (ChemCruz Biochemicals), and resveratrol, materials known in the art as capable of promoting or inducing SIRT1 expression can be used without limitation.

According to one example of the present disclosure, when resveratrol was treated at 20 µM, expressions of Six2 and WT1 were significantly promoted as compared with that of the control, thereby it was confirmed that the differentiation into the kidney precursor cell was promoted (see FIG. 3). Although resveratrol is preferably used in the present disclosure, a known SIRT1 expression promoter capable of promoting SIRT1 expression can be used without limitation, and SIRT1 specific sequences such as RNA promoting protein synthesis of SIRT1 can be synthesized and used.

The SIRT1 expression promoter may be added to the medium at a concentration of 5 to 50 µM, preferably 10 to 20 µM, when added at a concentration of 5 µM or less, there may be no inhibitory effect on the differentiation into kidney precursor cells, and when added at a concentration of 400 µM or more, cytotoxicity may be exhibited or efficiency may be decreased due to little improvement in efficacy by increased concentration.

Figure 7:
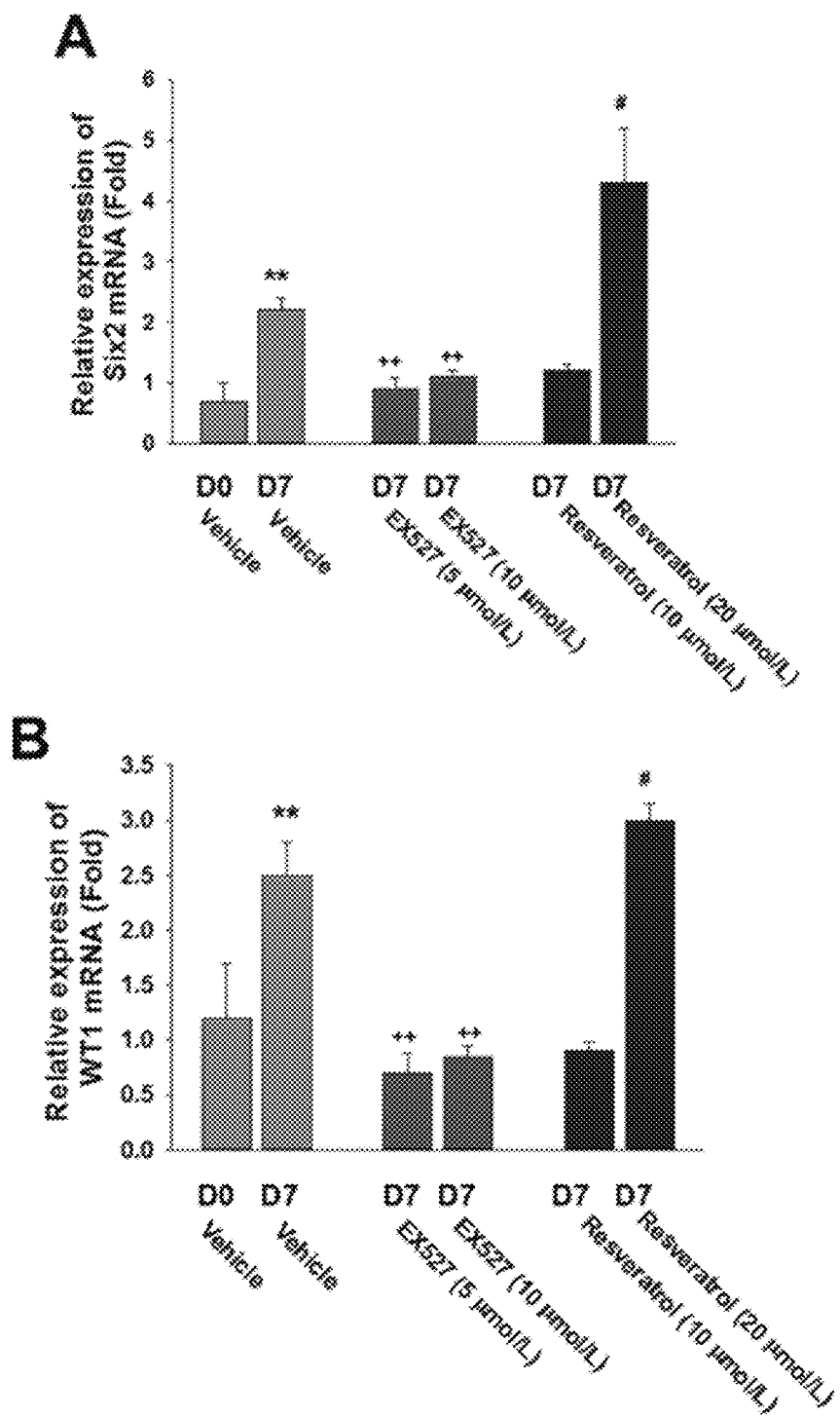
FIG. 7 shows an mRNA expression level of WT1 (A) and Six2 (B) which are kidney precursor cell indicators when embryonic stem cells were treated with the SIRT1 inhibitor EX527 (5-10 uM) and the SIRT1 promoter resveratrol (10-20 uM).

FIG. 7 is data obtained by measuring mRNA expression levels of WT1 (A) and Six2 (B) which are indicators of kidney precursor cell when EX527 (5-10 uM), a SIRT1 inhibitor, and resveratrol (10-20 uM), a SIRT1 promoter, were administered to embryonic stem cells. As described above, it might be confirmed that when the SIRT1 inhibitor was administered, the mRNA expression level of Six2 and WT1 was significantly decreased, and when resveratrol, a SIRT1 expression promoter, was administered, the mRNA expression level of Six2 and WT1 was significantly increased.

Referring to FIG. 8A and FIG. 8B, expressions of Six2 and WT1 were increased at 1 day of age in a wild-type mouse (Sirt1 co/co Hoxb7-Cre (−)), but expressions of Six2 and WT1 were decreased in a mouse (conditional knockout mouse: Sirt1 co/co; Hoxb7-Cre (+)) that specifically inhibited Sirt1 in renal collecting duct cells. This illustrates that the inhibition of SIRT1 can inhibit the differentiation of kidney precursor cells.

The SIRT1 expression promoter may be provided for 1 to 21 days from the induction of differentiation and most preferably may be provided from 1 to 7 days. When treated for a period shorter than 1 day, the effect of promoting or inhibiting the differentiation of kidney precursor cells may not be effective, and when treated for a period longer than 21 days, cell death may be exhibited due to cytotoxicity.

The present disclosure provides a kidney cell derived from a kidney precursor cell produced by the above method.

The present disclosure provides a renal function remedy or a therapeutic agent containing the kidney precursor cell produced by the above method.

The renal function remedy or the therapeutic agent of the present disclosure replenishes (regenerates) or reconstructs (restores) damaged kidney cells. The therapeutic agent may preferably be a cytotherapeutic agent.

"Regeneration" is a phenomenon in which a portion of formed organs or an individual is supplemented when it is lost, and "Restoration" can also be referred to as "reconstitution", referring to reconstruction of tissues or organs from dissociated cells or tissues.

This can be advantageously performed by direct implantation into the lesion site in the form of kidney cells or the composition containing the kidney cells (cytotherapeutic agent). Methods of neural transplantation and cell culture can be carried out using known methods well known to a person skilled in the art or the methods described in the examples of the present disclosure.

The term "treatment" or "treat" as used herein is a therapeutic treatment and preventative or prevention measure. Therefore, those in need of treatment include those with existing renal dysfunction. The methods of the present disclosure can be used to treat any mammal in need of treatment, including humans, primates and livestock, breeding, pet or sports animals such as dogs, horses, cats, sheep, pigs, cattle and the like, but are not limited to. As used herein, a "therapeutically effective amount" of a cell is an amount sufficient to stop or alleviate a patient's physiological effects caused by loss, damage or denaturation of differentiated kidney cells.

The therapeutically effective amount used of the cells will depend on the needs of the patient, the age, physiological condition and health of the patient, the predetermined therapeutic effect, the size and area of the tissue to be targeted for treatment, the severity of the lesion and the selected delivery route. For example, treatment of a disorder affecting a larger area of the brain may require more cells to achieve a therapeutic effect when compared to a smaller target area. In addition, the cell can be administered to one or more sites within a predetermined target tissue with multiple small grafts of a low cell dosage. A cell of the present disclosure can be completely isolated prior to transplantation, for example, to form a suspension of single cells, or to be almost completely isolated prior to transplantation, for example, to form a small aggregate of cells. The cell can be transplanted or transferred to a predetermined tissue site, can be administered in a manner that reconstitutes or regenerates a functionally deficient region.

The appropriate range of cells that can be administered to have a therapeutically effective effect can be suitably used in accordance with the patient within the ordinary knowledge of a person skilled in the art.

It should be understood, however, that the actual dosage should be determined in light of various relevant factors such as the disease to be treated, the route of administration, the age, sex and weight of the patient, and the severity of the disease, accordingly, the above dosage amounts do not limit the scope of the present disclosure in any way.

Hereinafter, the present disclosure will be described in more detail by way of examples. It will be apparent to a person skilled in the art that these examples are for illustrative only and that the scope of the present disclosure is not construed as being limited by these examples.

Example 1

Preparation and Culture of Mouse Embryonic Stem Cells

In the present disclosure, R1 cells which are embryonic stem cells were purchased from American Type Culture Collection (ATCC; ATCC SCRC-1011) and used, In order to determine whether a differentiation of embryonic stem cells into adipocytes was affected by the presence or absence of SIRT1 protein expression, the control which is embryonic stem cells (SIRT1+/+; WT) expressing the SIRT1 gene and mouse embryonic stem cells lacking SIRT1 genes (SIRT1−/−; KO) were prepared (Han M K et al., Cell Stem Cell., March 6; 2 (3): 241, 2008).

The mouse embryonic stem cells were cultured in Dulbecco's Modified Eagle's Medium (DMEM) supplemented with 2 mM GlutaMAX™ (Gibco, USA), 1× Non-essential amino acid (1×NEAA; Gibco, USA), 0.1 mM beta-mercaptoethanol (B-mercaptoethanol; Invitrogen, USA) and $10^3$ unit/ml leukemia inhibitory factor (LIF; Milipore, USA).

Example 2

Induced Differentiation of Mouse Embryonic Stem Cells into Adipocytes

In the present disclosure, in order to determine whether differentiation of embryonic stem cells into adipocytes was affected by the presence or absence of SIRT1 protein expression, degrees of differentiation of the embryonic stem cells (SIRT1+/+; WT) expressing the SIRT1 genes and the mouse embryonic stem cells lacking SIRT1 genes (SIRT1−/−; KO), prepared in Example 1, were determined, and when EX527 (10 μM, Tocris, UK), SIRT1 inhibitor, was treated with SIRT1+/+ embryonic stem cells, the degree of lipid differentiation according to SITRT1 inhibition was determined.

As shown in FIG. 1, experiments were carried out according to a culture protocol for differentiating embryonic stem cells into adipocytes, first, embryoid bodies were formed using a hanging-drop culture method, treated with retinoic acid for 3 days, and cultured for 14 days in a medium for inducing differentiation into adipocytes. In the hanging-drop culture, 1000 embryonic stem cells were added into 20 μl to prepare a single embryoid body, the process of induction into adipocytes was cultured by inoculating 15 cultures into each well using a 6-well plate.

The medium for differentiation into adipocyte was prepared by adding 85 nM insulin (Sigma, USA), 2 nM triiodothyronine (Sigma, USA) and 2 μM rosiglitazone (Sigma, USA) to DMEM and embryoid bodies were cultured, the medium exchange was performed daily.

In addition, SIRT1 inhibitor EX527 was added to SIRT1+/+ embryonic stem cells until the early 5th day of differentiation into adipocytes.

Example 3

Identification of Differentiation of Embryonic Stem Cells into Adipocytes by Oil Red O Staining Oil Red O staining was performed to determine whether the differentiation into adipocytes was successfully performed in mouse embryonic stem cells differentiated for 21 days in Example 2.

First, SIRT1+/+ cells, SIRT1−/− cells, and SIRT1+/+ cells differentiated by treatment with SIRT1 inhibitor were treated with 10% formaldehyde to fix the cells, the formaldehyde was washed with phosphate buffered saline three times and then was treated with 60% isopropanol. Then, 2 ml Oil Red O staining solution was added and the mixture was stained at room temperature for 30 minutes in the dark, and then was washed with phosphate buffered saline three times.

The stained cells were observed with a microscope. Oil Red O staining was performed on the lipid droplets in the differentiated adipocytes. After staining, the cells were observed using a microscope to identify red-stained fat adipocytes.

When the observation was completed, stained dye in adipocyte was extracted using 1 ml isopropanol per well and optical density (OD) was measured at 500 nm with an ELISA reader. The Oil Red O staining solution is a solution of 500 mg of Oil Red O dye (Sigma, USA) in 100 ml isopropanol, mixed with distilled water at a ratio of 6:4 and filtered using a 0.45 μm filter.

As a result, as shown in FIG. 2A, it was confirmed that embryonic stem cells were differentiated into adipocytes in SIRT1+/+ cells, and many intracellular lipid droplets were formed. On the other hand, it was confirmed that there was almost no differentiation into adipocytes in SIRT1−/− cells. In addition, when SIRT1+/+ cells were treated with the SIRT1 inhibitor EX527, it was confirmed that adipocyte differentiation was remarkably lower than that of SIRT1+/+ cells although lipid droplets were partially observed.

FIG. 2B is data obtained by measuring absorbance at 500 nm after extracting oil red O samples stained in lipid droplets of cells. It was confirmed that SIRT1−/− cells were reduced by 40% in differentiation into adipocytes compared to SIRT1+/+ cells. In addition, when EX527, SIRT1 inhibitor, was treated, it was confirmed that adipocyte differentiation was reduced by about 38%.

Example 4

Confirmation of Mechanism of Regulation of Differentiation into Adipocyte by SIRT1

In the present disclosure, in order to confirm the mechanism of regulating the differentiation of embryonic stem cells into adipocytes by SIRT1, in the step of differentiating into adipocytes, mRNA expression levels of peroxisome proliferator-activated receptors-γ (PPARγ), CCAAT/enhancer-binding protein-α (C/EBP α) and fatty acid binding protein 4 (FABP4) in adipocytes were measured by a PCR method. Each primer used in the PCR method was as represented in Table 1 and was manufactured by Bioneer (Korea). GAPDH was used as a control group for the reliability of the PCR method.

TABLE 1

Primer sequence

| Primer | | Sequence (5'→3') | | Tm (° C.) |
|---|---|---|---|---|
| PPARγ | Forward | TGTGAGACCAA CAGCCTGAC | SEQ ID NO: 2 | 60 |
| | Reverse | AGCTGATTCCG AAGTTGGTG | SEQ ID NO: 3 | |
| C/EBP α | Forward | TGGACAAGAAC AGCAACGAG | SEQ ID NO: 4 | 60 |
| | Reverse | AAACCATCCTC TGGGTCTCC | SEQ ID NO: 5 | |
| FABP4 | Forward | AATGTGTGATG CCTTTGTGG | SEQ ID NO: 6 | 60 |
| | Reverse | TCGACTTTCCA TCCCACTTC | SEQ ID NO: 7 | |
| GAPDH | Forward | AGGTCGGTGTG AACGGATTTG | SEQ ID NO: 8 | 60 |
| | Reverse | GGGGTCGTTGA TGGCAACA | SEQ ID NO: 9 | |

In the same manner as in Example 2, differentiation of embryonic stem cells into adipocytes was induced, each cell was harvested on 7 and 10 days after induction of lipid differentiation, and total RNAs were extracted using TRIzol reagent (Life Technology, USA). The extracted RNAs were synthesized into cDNAs using a cDNA synthesis kit (Roche, Germany) and a PCR method was carried out using the primers represented in Table 1.

As a result, it was confirmed that mRNA expressions of PPARγ, C/EBP α and FABP4 were increased in SIRT1+/+ cells after induction of differentiation into adipocytes. On the other hand, it was confirmed that mRNA expressions of PPARγ, C/EBP α and FABP4 were significantly decreased when SIRT1−/− cells and EX527, SIRT1 inhibitor, were treated.

In other words, it was confirmed that, when the expression of SIRT1 was inhibited, in the differentiation of embryonic stem cells into adipocytes, mRNA expressions of intracellular PPARγ, C/EBPα, and FABP4 were decreased and the differentiation into adipocytes were decreased. This means that increasing the expression of SIRT1 promotes the differentiation of embryonic stem cells into adipocytes.

Example 5

Confirmation of the Degree of Differentiation into Adipocytes by SIRT1 Inhibition In the present disclosure, in order to confirm the effect on a differentiation of embryonic stem cells into adipocytes according to time (or period) of inhibition of SIRT1 expression, EX527 (10 μM), the SIRT1 inhibitor, was treated according to time.

In the same manner as in Example 2, differentiation of embryonic stem cells into adipocytes was induced. The samples were divided into various groups: a group treated for 0 to 5 days at the early stage of differentiation, a group treated for 7 to 21 days at the latter stage of differentiation, and a group treated for 0 to 21 days during the entire differentiation period, which were treated with the SIRT1 inhibitor. Afterwards, Oil Red O staining was performed in the same manner as in Example 3 to confirm the degrees of differentiation into adipocytes.

As a result, as shown in FIG. 4, it was confirmed that the group treated with the SIRT1 inhibitor only at the early stage of differentiation showed a decrease in differentiation into adipocytes compared to the groups that were not treated with the inhibitor. However, the group treated with the SIRT1 inhibitor during the entire differentiation period was not significantly different from the groups without inhibitor treatment, and the group treated with inhibitor during 7-21 days, at the latter stage of the differentiation, was more differentiated into adipocytes than the groups without inhibitor treatment.

It was conformed that the inhibition or promotion of differentiation into adipocyte can be induced according to the time of inhibition of SIRT1 expression. It was confirmed that, when SIRT1 expression was inhibited at the early stage of culturing of embryoid body formed from embryonic stem cell, the differentiation into adipocyte was inhibited by inhibition of SIRT1, unlike previous knowledge in the art. It was confirmed that the differentiation into the adipocyte was promoted when SIRT1 expression was inhibited during 7 to 21 days in induction of differentiation of the embryoid body into adipocyte.

Example 6

Induction of Differentiation of Mouse Embryonic Stem Cell into Kidney Precursor Cell In the present disclosure, in order to determine whether differentiation of embryonic stem cells into kidney precursor cells was affected by the presence or absence of SIRT1 protein expression, differentiation of the embryonic stem cells (SIRT1+/+; WT) expressing the SIRT1 genes and the mouse embryonic stem cells lacking SIRT1 genes (SIRT1−/−; KO), which were prepared in Example 1, was induced.

As shown in FIG. 5, experiments were carried out according to a culture protocol for differentiating embryonic stem cells into kidney precursor cells. The cell culture media, from which Leukemia Inhibitory Factor (LIF; Milipore, USA) was removed, were treated with 100 nmol/L Retinoic acid and 10 ng/mL Activin A, and then mRNA expression levels of Six2 and WT1, kidney precursor cells, were measured. In the process of induction into kidney precursor cells, embryonic stem cells were inoculated into wells of a 6-well plate to be cultured therein.

The media for differentiation into kidney precursor cells were cultured by adding 2 mM Gluta MAX™ (Gibco, USA), 1× Non-essential aminoacid, (1×NEAA; Gibco, USA), 0.1 mM beta-mercaptoethanol (Invitrogen, USA) and 1,000 unit/ml Leukemia Inhibitory Factor (LIF; Milipore, USA) to DMEM.

Example 7

Confirmation of Differentiation of Embryonic Stem Cells into Kidney Precursor Cells Through mRNA Expression Level In order to confirm the differentiation of embryonic stem cells into kidney precursor cells according to the presence or absence of SIRT1 protein expression, the differentiation of the embryonic stem cells (SIRT1+/+; WT) expressing the SIRT1 genes and the mouse embryonic stem cells lacking SIRT1 genes (SIRT1−/−; KO), which were prepared in Example 1, into kidney precursor cells were confirmed. The differentiation was confirmed by mRNA expression levels of Six2 and WT1, indicators of kidney precursor cells.

In the step for differentiation of embryonic stem cells into kidney precursor cells, mRNA expression levels of Six2 and WT1, indicators of kidney precursor cells, were measured by a PCR method. Each primer used in the PCR method was as represented in Table 2 and was manufactured by Bioneer (Korea). GAPDH was used as a control group for the reliability of the PCR method.

TABLE 2

Primer sequence

| Primer | | Sequence (5'→3') | | Tm (° C.) |
|---|---|---|---|---|
| Six2 | Forward | CAAGGAAAGGG AGAACAGCGA | SEQ ID NO: 10 | 60 |
| | Reverse | GCGTCTTCTCA TCCTCGGAA | SEQ ID NO: 11 | |
| WT1 | Forward | ATCCCAGGCAG GAAAGTGTG | SEQ ID NO: 12 | 60 |
| | Reverse | GTGCTGTCTTG GAAGTCGGA | SEQ ID NO: 13 | |
| GAPDH | Forward | AGGTCGGTGTG AACGGATTTG | SEQ ID NO: 14 | 60 |
| | Reverse | GGGGTCGTTGA TGGCAACA | SEQ ID NO: 15 | |

In the same manner as in Example 6, differentiation of embryonic stem cells into kidney precursor cells was induced, each cell was harvested on day 11 of differentiation induction and then total RNAs were extracted using TRIzol reagent (Life Technology, USA). The extracted RNAs were synthesized into cDNAs using a cDNA synthesis kit (Roche, Germany) and a PCR method was carried out using the primers represented in Table 2.

As a result, as shown in FIG. 6, in SIRT1−/− cells, it was confirmed that mRNA expressions of Six2 and WT1 were inhibited after induction of differentiation into kidney precursor cells. On the other hand, in SIRT1+/+ cells, it was confirmed that mRNA expressions of Six2 and WT1 were significantly increased.

In other words, it was confirmed that, when expression of SIRT1 was inhibited, in the differentiation of embryonic stem cells into kidney precursor cells, mRNA expressions of Six2 and WT1 in the cells were decreased and the differentiation into kidney precursor cells were decreased. This means that the differentiation of embryonic stem cells into kidney precursor cells is inhibited when the expression of SIRT1 is inhibited.

Example 8

Confirmation of a Regulation of Differentiation of Embryonic Stem Cell into Kidney Precursor Cell Through SIRT1 Inhibition and Activation In order to confirm the differentiation of embryonic stem cells into kidney precursor cells according to the inhibition or promotion of SIRT1 protein expression, the differentiation of the embryonic stem cells (SIRT1+/+; WT) expressing the SIRT1 genes, which were prepared in Example 1, into kidney precursor cells was confirmed. The differentiation was confirmed by protein expression levels of Six2 and WT1, indicators of kidney precursor cells.

In the step for differentiation of embryonic stem cells into kidney precursor cells, mRNA expression levels of Six2 and WT1, indicators of kidney precursor cells, were measured by a quantitative PCR method.

As a result, as shown in FIG. 7, it can be appreciated that mRNA expression level (A) of WT1 and mRNA expression level (B) of Six2 were decreased by administration of SIRT1 inhibitor, and that mRNA expression levels of Six2 and WT1 were increased by administration of resveratrol stimulating SIRT1 expression. This means that differentiation into kidney precursor cells are promoted when the SIRT1 protein expression is increased.

Example 9

Confirmation of Differentiation into Kidney Precursor Cell when SIRT1 Expression is Inhibited Changes in protein expression of Six2 and WT1 were observed in mouse fetal kidney (conditional knockout mouse: Sirt1 co/co; Hoxb7-Cre (+)) at the first day of birth by specifically inhibiting SIRT1 protein in renal collecting duct cells.

Changes in protein expressions of Six2 and WT1 were measured by immunofluorescence staining. For immunochemical staining, a kidney was extracted from a pregnant mouse or a mouse of the 0th day of birth, was fixed with 4% paraformaldehyde for 6 hours, and then was cut at a thickness of 10 mm to be used for staining. Used antibodies were Anti-Six2 (Abcam; ab68908, Cambridge, UK), Anti-WT1 (Abcam; Cambridge, UK), a Zeiss Z1 microscope and a Zeiss LSM 510 confocal microscope (Carl Zeiss, Germany).

Figure 8:
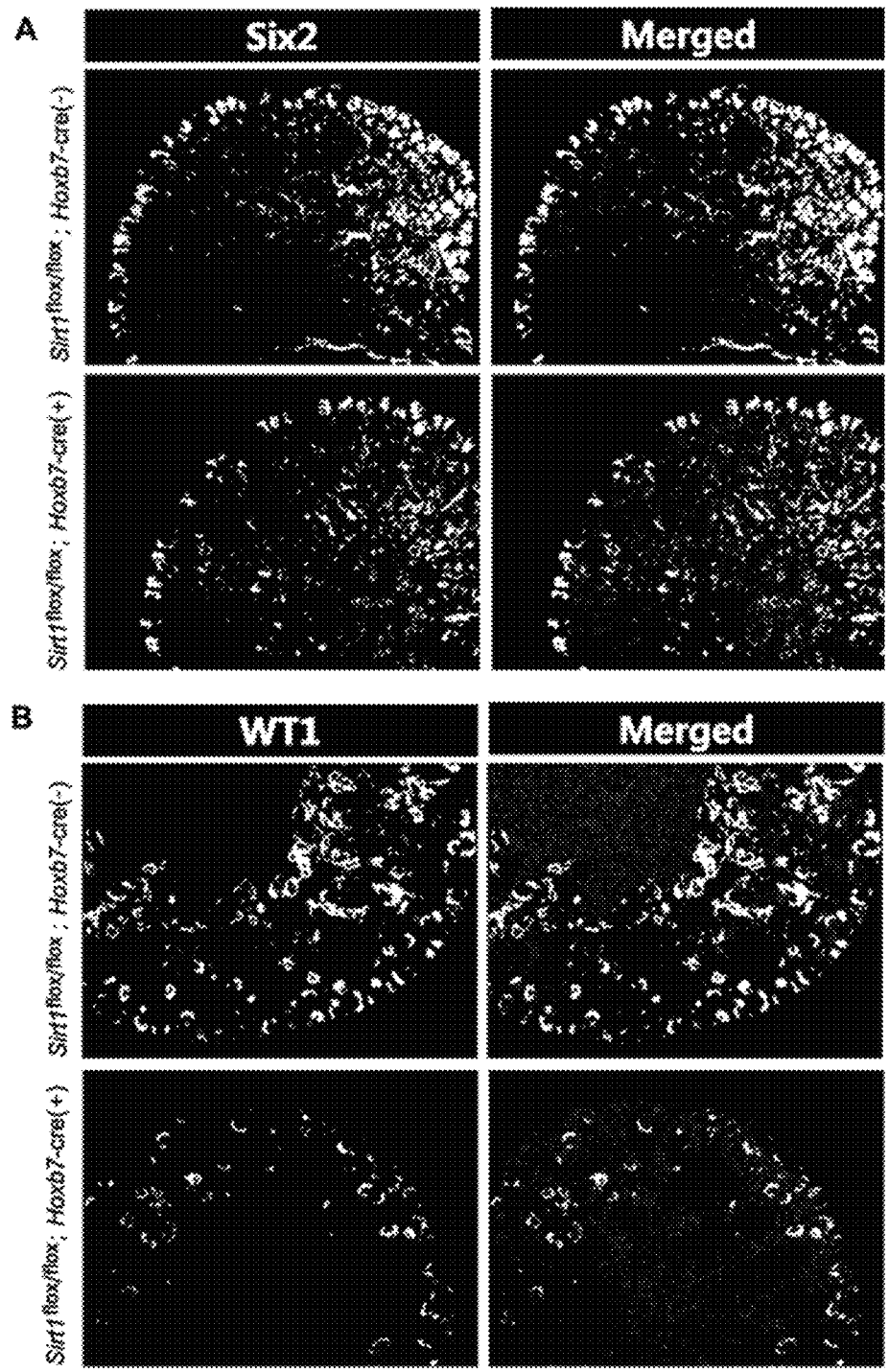
FIG. 8 is immunofluorescence staining data obtained by measuring expression position of Six2 (FIG. 4A) and WT1 (FIG. 4B) at 1 day of age in a mouse (conditional knockout mouse: Sirt1 co/co; Hoxb7-Cre (+)) that specifically inhibited Sirt1 in renal collecting duct cell and a wild-type mouse (Sirt1 co/co Hoxb7-Cre (−)).
Figure 9:
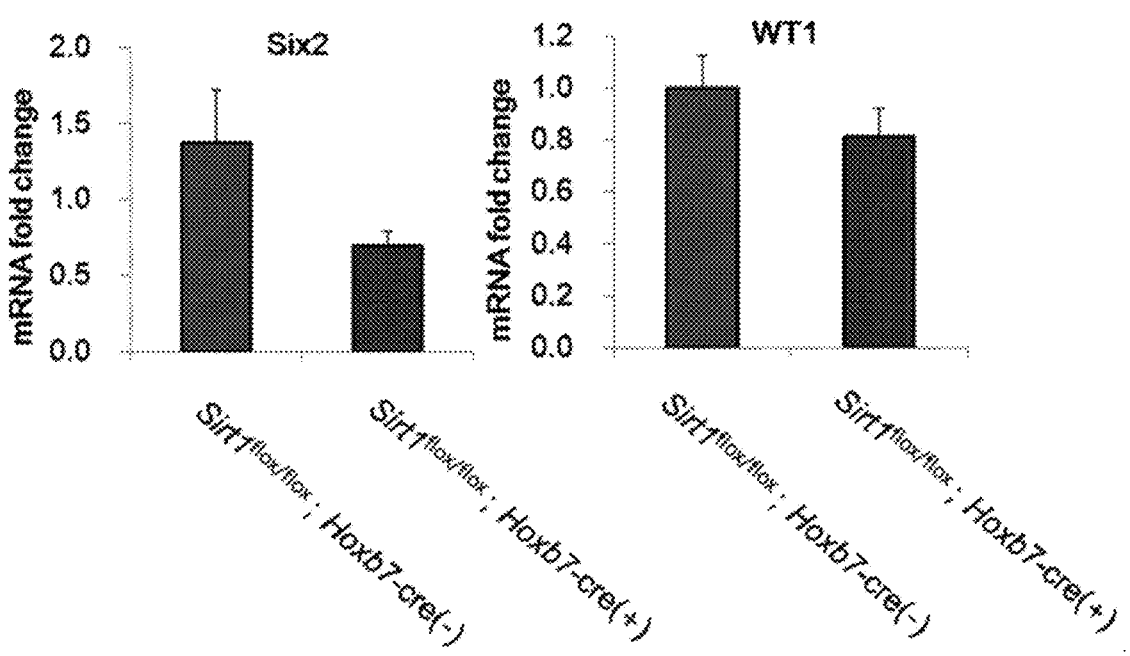
FIG. 9 is quantitative RT-PCR data obtained by measuring degree of mRNA expression of Six2 (FIG. 4A) and WT1 (FIG. 4B) at 1 day of age in a mouse (conditional knockout mouse: Sirt1 co/co; Hoxb7-Cre (+)) that specifically inhibited Sirt1 in renal collecting duct cell and a wild-type mouse (Sirt1 co/co Hoxb7-Cre (−)).

As a result, as shown in FIG. 8 and FIG. 9, in the group in which SIRT1 protein was specifically inhibited in kidney collecting duct cells, it could be confirmed that the differentiation into kidney precursor cells was decreased compared to the other groups. This means that even when mRNA or protein is not expressed due to deficiency of SIRT1, differentiation into kidney precursor cells can be inhibited.

What is claimed is:

1. A method for inhibiting a differentiation of embryonic stem cells into adipocytes, the method comprising the steps of:
   (a) forming an embryoid body by culturing embryonic stem cells;
   (b) culturing the embryoid body with a silent mating type information regulation 2 homolog (SIRT1) expression inhibitor for 1, 2, 3, 4, or 5 days; and
   (c) replacing a medium used in the culturing of step (b) with a medium without the SIRT1 expression inhibitor, wherein the culturing of step (b) prevents the embryoid body from differentiating into an adipocyte.

2. The method of claim 1, wherein the SIRT1 expression inhibitor is any one selected from the group consisting of 2-[(2-Hydroxynaphthalen-1-ylmethylene)amino]-N-(1-phenethyl)benzamide, a pyridine-3-carboxamide, and 6-Chloro-2,3,4,9-tetrahydro-1H-Carbazole-1-carboxamide.

3. The method of claim 1, wherein mRNA expressions of a peroxisome proliferator-activated receptors-γ (PPAR-γ), a CCAAT/enhancer-binding protein-α (C/EBP α), a fatty acid binding protein 4 (FABP4), a sine oculis homeobox homolog 2 (SIX2), and a wilms tumor 1 (WT1) are decreased by the SIRT1 expression inhibitor.

4. A method for promoting a differentiation of embryonic stem cells into adipocytes, the method comprising the steps of:
   (a) forming an embryoid body by culturing embryonic stem cells;
   (b) culturing the embryoid body without a SIRT1 expression inhibitor for 1, 2, 3, 4, or 5 days; and (c) culturing the embryoid body with a SIRT1 expression inhibitor from 14 to 21 days, wherein the culturing of step (c) promotes the embryoid body to differentiate into an adipocyte.

5. The method of claim 4, wherein the SIRT1 expression inhibitor is any one selected from the group consisting of 2-[(2-Hydroxynaphthalen-1-ylmethylene)amino]-N-(1-phenethyl)benzamide, a pyridine-3-carboxamide, and 6-Chloro-2,3,4,9-tetrahydro-1H-Carbazole-1-carboxamide.

6. The method of claim 4, wherein a medium used in the culturing of step (c) is a medium for inducing the differentiation into adipocytes, and comprises at least one selected from the group consisting of insulin, triiodothyronine, and rosiglitazone.

7. A method for promoting a differentiation of embryonic stem cells into kidney precursor cells, the method comprising the step of:

(a) culturing embryonic stem cells with at least 20 μmol/L of a resveratrol, wherein the culturing promotes the differentiation of the embryonic stem cell into a kidney precursor cell.

8. The method of claim 7, wherein the resveratrol is treated from 1 to 21 days.

* * * * *

SEQUENCE LISTING

```
<160> NUMBER OF SEQ ID NOS: 15

<210> SEQ ID NO 1
<211> LENGTH: 2214
<212> TYPE: DNA
<213> ORGANISM: Artificial
<220> FEATURE:
<223> OTHER INFORMATION: sirt1 gene

<400> SEQUENCE: 1
atggcggacg aggtggcgct cgcccttcag gccgccggct ccccttccgc ggcggccgcc      60
atggaggccg cgtcgcagcc ggcggacgag ccgctccgca agaggccccg ccgagacggg     120
cctggcctcg ggcgcagccc gggcgagccg agcgcagcag tggcgccggc ggccgcgggg     180
tgtgaggcgg cgagcgccgc ggccccggcg gcgctgtggc gggaggcggc aggggcggcg     240
gcgagcgcgg agcgggaggc cccggcgacg gccgtggccg gggacggaga caatgggtcc     300
ggcctgcggc gggagccgag ggcggctgac gacttcgacg acgacgaggg cgaggaggag     360
gacgaggcgg cggcggcagc ggcggcggca gcgatcggct accgagacaa cctcctgttg     420
accgatggac tcctcactaa tggctttcat tcctgtgaaa gtgatgacga tgacagaacg     480
tcacacgcca gctctagtga ctggactccg cggccgcgga taggtccata tactttttgtt    540 cagcaacatc tcatgattgg caccgatcct cgaacaattc ttaaagattt attaccagaa     600
acaattcctc cacctgagct ggatgatatg acgctgtggc agattgttat taatatcctt     660
tcagaaccac caaagcggaa aaaaagaaaa gatatcaata caattgaaga tgctgtgaag     720
```

| | |
|---|---|
| ttactgcagg agtgtaaaaa gataatagtt ctgactggag ctggggtttc tgtctcctgt | 780 |
| gggattcctg acttcagatc aagagacggt atctatgctc gccttgcggt ggacttccca | 840 |
| gacctcccag accctcaagc catgtttgat attgagtatt ttagaaaaga cccaagacca | 900 |
| ttcttcaagt ttgcaaagga aatatatccc ggacagttcc agccgtctct gtgtcacaaa | 960 |
| ttcatagctt tgtcagataa ggaaggaaaa ctacttcgaa attatactca aaatatagat | 1020 |
| accttggagc aggttgcagg aatccaaagg atccttcagt gtcatggttc ctttgcaaca | 1080 |
| gcatcttgcc tgatttgtaa atacaaagtt gattgtgaag ctgttcgtgg agacattttt | 1140 |
| aatcaggtag ttcctcggtg ccctaggtgc ccagctgatg agccacttgc catcatgaag | 1200 |
| ccagagattg tcttctttgg tgaaaactta ccagaacagt ttcatagagc catgaagtat | 1260 |
| gacaaagatg aagttgacct cctcattgtt attggatctt ctctgaaagt gagaccagta | 1320 |
| gcactaattc caagttctat accccatgaa gtgcctcaaa tattaataaa tagggaacct | 1380 |
| ttgcctcatc tacattttga tgtagagctc cttggagact gcgatgttat aattaatgag | 1440 |
| ttgtgtcata ggctaggtgg tgaatatgcc aaactttgtt gtaaccctgt aaagctttca | 1500 |
| gaaattactg aaaaacctcc acgcccacaa aaggaattgg ttcatttatc agagttgcca | 1560 |
| ccaacacctc ttcatatttc ggaagactca agttcacctg aaagaactgt accacaagac | 1620 |
| tcttctgtga ttgctacact tgtagaccaa gcaacaaaca acaatgttaa tgatttagaa | 1680 |
| gtatctgaat caagttgtgt ggaagaaaaa ccacaagaag tacagactag taggaatgtt | 1740 |
| gagaacatta atgtggaaaa tccagatttt aaggctgttg gttccagtac tgcagacaaa | 1800 |
| aatgaaagaa cttcagttgc agaaacagtg agaaaatgct ggcctaatag acttgcaaag | 1860 |
| gagcagatta gtaagcggct tgagggtaat caatacctgt ttgtaccacc aaatcgttac | 1920 |
| atattccacg gtgctgaggt atactcagac tctgaagatg acgtcttgtc ctctagttcc | 1980 |
| tgtggcagta acagtgacag tggcacatgc cagagtccaa gtttagaaga acccttggaa | 2040 |
| gatgaaagtg aaattgaaga attctacaat ggcttggaag atgatacgga gaggcccgaa | 2100 |
| tgtgctggag atctggatt tggagctgat ggagggatc aagaggttgt taatgaagct | 2160 |
| atagctacaa gacaggaatt gacagatgta aactatccat cagacaaatc ataa | 2214 |

<210> SEQ ID NO 2
<211> LENGTH: 20
<212> TYPE: DNA
<213> ORGANISM: Artificial
<220> FEATURE:
<223> OTHER INFORMATION: PPAR gamma forward primer

<400> SEQUENCE: 2
tgtgagacca acagcctgac                                           20

<210> SEQ ID NO 3
<211> LENGTH: 20
<212> TYPE: DNA
<213> ORGANISM: Artificial
<220> FEATURE:
<223> OTHER INFORMATION: PPAR gamma reverse primer

<400> SEQUENCE: 3
agctgattcc gaagttggtg                                           20

<210> SEQ ID NO 4
<211> LENGTH: 20
<212> TYPE: DNA
<213> ORGANISM: Artificial

```
<220> FEATURE:
<223> OTHER INFORMATION: C/EBP alpha forward primer

<400> SEQUENCE: 4
tggacaagaa cagcaacgag                                               20

<210> SEQ ID NO 5
<211> LENGTH: 20
<212> TYPE: DNA
<213> ORGANISM: Artificial
<220> FEATURE:
<223> OTHER INFORMATION: C/EBP alpha reverse primer

<400> SEQUENCE: 5
aaaccatcct ctgggtctcc                                               20

<210> SEQ ID NO 6
<211> LENGTH: 20
<212> TYPE: DNA
<213> ORGANISM: Artificial
<220> FEATURE:
<223> OTHER INFORMATION: FABP4 forward primer

<400> SEQUENCE: 6
aatgtgtgat gcctttgtgg                                               20

<210> SEQ ID NO 7
<211> LENGTH: 20
<212> TYPE: DNA
<213> ORGANISM: Artificial
<220> FEATURE:
<223> OTHER INFORMATION: FABP4 reverse primer

<400> SEQUENCE: 7
tcgactttcc atcccacttc                                               20

<210> SEQ ID NO 8
<211> LENGTH: 21
<212> TYPE: DNA
<213> ORGANISM: Artificial
<220> FEATURE:
<223> OTHER INFORMATION: GAPDH forward primer

<400> SEQUENCE: 8
aggtcggtgt gaacggattt g                                             21

<210> SEQ ID NO 9
<211> LENGTH: 19
<212> TYPE: DNA
<213> ORGANISM: Artificial
<220> FEATURE:
<223> OTHER INFORMATION: GAPDH reverse primer

<400> SEQUENCE: 9
ggggtcgttg atggcaaca                                                19

<210> SEQ ID NO 10
<211> LENGTH: 21
<212> TYPE: DNA
<213> ORGANISM: Artificial
<220> FEATURE:
<223> OTHER INFORMATION: six2 forward primer

<400> SEQUENCE: 10
caaggaaagg gagaacagcg a                                             21
```

```
<210> SEQ ID NO 11
<211> LENGTH: 20
<212> TYPE: DNA
<213> ORGANISM: Artificial
<220> FEATURE:
<223> OTHER INFORMATION: six2 reverse primer

<400> SEQUENCE: 11
gcgtcttctc atcctcggaa                                              20

<210> SEQ ID NO 12
<211> LENGTH: 20
<212> TYPE: DNA
<213> ORGANISM: Artificial
<220> FEATURE:
<223> OTHER INFORMATION: WT1 forward primer

<400> SEQUENCE: 12
atcccaggca ggaaagtgtg                                              20

<210> SEQ ID NO 13
<211> LENGTH: 20
<212> TYPE: DNA
<213> ORGANISM: Artificial
<220> FEATURE:
<223> OTHER INFORMATION: WT1 reverse primer

<400> SEQUENCE: 13
gtgctgtctt ggaagtcgga                                              20

<210> SEQ ID NO 14
<211> LENGTH: 21
<212> TYPE: DNA
<213> ORGANISM: Artificial
<220> FEATURE:
<223> OTHER INFORMATION: GAPDH forward primer

<400> SEQUENCE: 14
aggtcggtgt gaacggattt g                                            21

<210> SEQ ID NO 15
<211> LENGTH: 19
<212> TYPE: DNA
<213> ORGANISM: Artificial
<220> FEATURE:
<223> OTHER INFORMATION: GAPDH reverse primer

<400> SEQUENCE: 15
ggggtcgttg atggcaaca                                               19
```